United States Patent
Hudgins et al.

(10) Patent No.: US 11,191,921 B1
(45) Date of Patent: Dec. 7, 2021

(54) CONVECTION AROMATHERAPY DEVICE (71) Applicants: David Hudgins, Carthage, MS (US); George R. Breiwa, III, Dane, WI (US)

(72) Inventors: David Hudgins, Carthage, MS (US); George R. Breiwa, III, Dane, WI (US)

(73) Assignees: DynaVap, LLC, DeForest, WI (US); Eds TNT LLC, Carthage, MS (US)

( * ) Notice: Subject to any disclaimer, the term of this patent is extended or adjusted under 35 U.S.C. 154(b) by 66 days.

(21) Appl. No.: 16/289,282

(22) Filed: Feb. 28, 2019

Related U.S. Application Data (60) Provisional application No. 62/636,585, filed on Feb. 28, 2018.

(51) Int. Cl.
*A61L 9/03* (2006.01)
*A61M 21/00* (2006.01)
*A61M 11/04* (2006.01)

(52) U.S. Cl.
CPC .......... *A61M 21/00* (2013.01); *A61M 11/045* (2014.02); *A61M 2021/0016* (2013.01); *A61M 2205/127* (2013.01); *A61M 2205/362* (2013.01); *A61M 2205/3653* (2013.01)

(58) Field of Classification Search
CPC ................ A61M 21/00; A61M 11/045; A61M 2205/3653; A61M 2205/362; A61M 2205/127; A61M 2021/0016
See application file for complete search history.

(56) References Cited

U.S. PATENT DOCUMENTS

| | | | | |
|---|---|---|---|---|
| 2,300,891 | A * | 11/1942 | Hanks | A47J 36/2433 392/336 |
| 3,890,486 | A * | 6/1975 | Fitzgerald | A01K 63/065 219/523 |
| 4,819,625 | A * | 4/1989 | Howe | A61M 16/16 128/200.14 |
| 5,388,594 | A * | 2/1995 | Counts | A24F 47/008 128/202.21 |
| 5,878,752 | A * | 3/1999 | Adams | A24F 47/008 131/329 |
| 6,095,153 | A * | 8/2000 | Kessler | A24F 47/008 131/194 |
| 6,444,956 | B1 * | 9/2002 | Witcher | A45D 34/00 219/386 |
| 10,206,425 | B2 | 2/2019 | Breiwa, III | |
| 2003/0000939 | A1 * | 1/2003 | Faries, Jr. | A61M 5/445 219/497 |
| 2003/0150451 | A1 * | 8/2003 | Shayan | A24F 47/008 128/203.12 |
| 2008/0179311 | A1 * | 7/2008 | Koro | A47J 36/2416 219/430 |
| 2009/0095287 | A1 * | 4/2009 | Emarlou | A61M 11/041 128/200.14 |
| 2009/0107980 | A1 * | 4/2009 | Andel | A61M 16/024 219/443.1 |

(Continued)

*Primary Examiner* — Regina M Yoo
(74) *Attorney, Agent, or Firm* — Boardman & Clark LLP (57) ABSTRACT

A convection aromatherapy device is disclosed. The device has a body made of a suitable material, an air path for transfer of heat, and an electric cartridge heater. A source of heat, and/or hot air and device or means for selective vaporization of desirable compounds from various materials is thereby provided. A kit for convection aromatherapy is also provided.

8 Claims, 12 Drawing Sheets

(56) References Cited

U.S. PATENT DOCUMENTS

| | | | | |
|---|---|---|---|---|
| 2011/0308521 A1* | 12/2011 | Kofford | ............... | A61M 11/044 |
| | | | | 128/203.27 |
| 2017/0013877 A1* | 1/2017 | Breiwa, III | ........... | A61M 15/06 |
| 2019/0320717 A1* | 10/2019 | Tabasso | .................. | A24F 40/50 |

\* cited by examiner

CONVECTION AROMATHERAPY DEVICE

CROSS-REFERENCE TO RELATED APPLICATIONS

This application claims priority to U.S. Provisional Patent Application, Ser. No. 62/636,585, filed Feb. 28, 2018, entitled "Convection Aromatherapy Device" the entire contents of which is hereby incorporated by reference herein in its entirety.

FIELD

The present inventions relate to the field of aromatherapy devices. More specifically, the present inventions relate to the field of convection aromatherapy devices.

BACKGROUND

Aromatherapy devices are known. Aromatherapy, often called an essential oil therapy, is a holistic healing treatment that often uses natural plant extracts and scents to promote health and well-being. A variety of devices exist designed to release these scents into the air, such as diffusers, aromatic spritzers, inhalers, steamers, and so forth.

"Vaping" or the inhalation of vaporized substances using a vaporizer, electronic cigarette, or similar device, has become increasingly popular since its introduction to the market a short time ago. Current devices such as vaporizers and electronic cigarettes function via an electrically heated and controlled vaporization element. This allows for a very precise level of control, but forces complete reliance upon electricity, batteries, charging devices, and connectors. Although battery technology continues to improve and evolve, volumetrically batteries can only store a small fraction of the energy stored in most fuels.

Known aromatherapy devices and vaporization devices have a number of deficiencies including one or more of the following: long heat-up times, inability to retain heat, prolonged recovery time, insufficient extraction of desirable compounds, housing degradation, inferior components, restricted air flow, inefficient use of available power, significant heat loss, damage to interior structures due to uncontrolled thermal conduction, electrical risk power source issues, cumbersome form factors, difficulty functioning in harsh environmental conditions, and so forth.

Accordingly, a need exists for an improved device that solves one or more of the deficiencies of existing devices. More specifically, a need exists for a device that has improved airflow and is constructed of materials with better thermal properties in conjunction with thermal isolation. A need also exists for a convection aromatherapy device that may also be used in connection with vaporization.

SUMMARY

Accordingly, a convection aromatherapy device is disclosed. The device has a body made of a suitable material, an air path for transfer of heat, and an electric cartridge heater. The general purpose is to provide a source of heat, and/or hot air for selective vaporization of desirable compounds from various materials.

An additional convection aromatherapy device is disclosed. The device has a body formed by an annular wall and a base creating a recessed area. A cartridge heater is provided within the recessed area. An air path is also provided for transfer of heat from the cartridge heater.

A kit for convection aromatherapy is also provided. The kit includes a convection aromatherapy device having a body formed by an annular wall and a base creating a recessed area, a cartridge heater within the recessed area, and an air path for transfer of heat from the cartridge heater. The kit also includes a power cord coupleable to the cartridge heater for delivering power to the heater and a temperature control joined to the power cord.

These and other features and advantages of devices, systems, and methods according to this invention are described in, or are apparent from, the following detailed descriptions of various examples of embodiments.

BRIEF DESCRIPTION OF DRAWINGS

Various examples of embodiments of the systems, devices, and methods according to this invention will be described in detail, with reference to the following figures, wherein.

It should be understood that the drawings are not necessarily to scale. In certain instances, details that are not necessary to the understanding of the invention or render other details difficult to perceive may have been omitted. For ease of understanding and simplicity, common numbering of elements within the numerous illustrations is utilized when the element is the same in different Figures. It should be understood, of course, that the invention is not necessarily limited to the particular embodiments illustrated herein.

DETAILED DESCRIPTION

Figure 1:
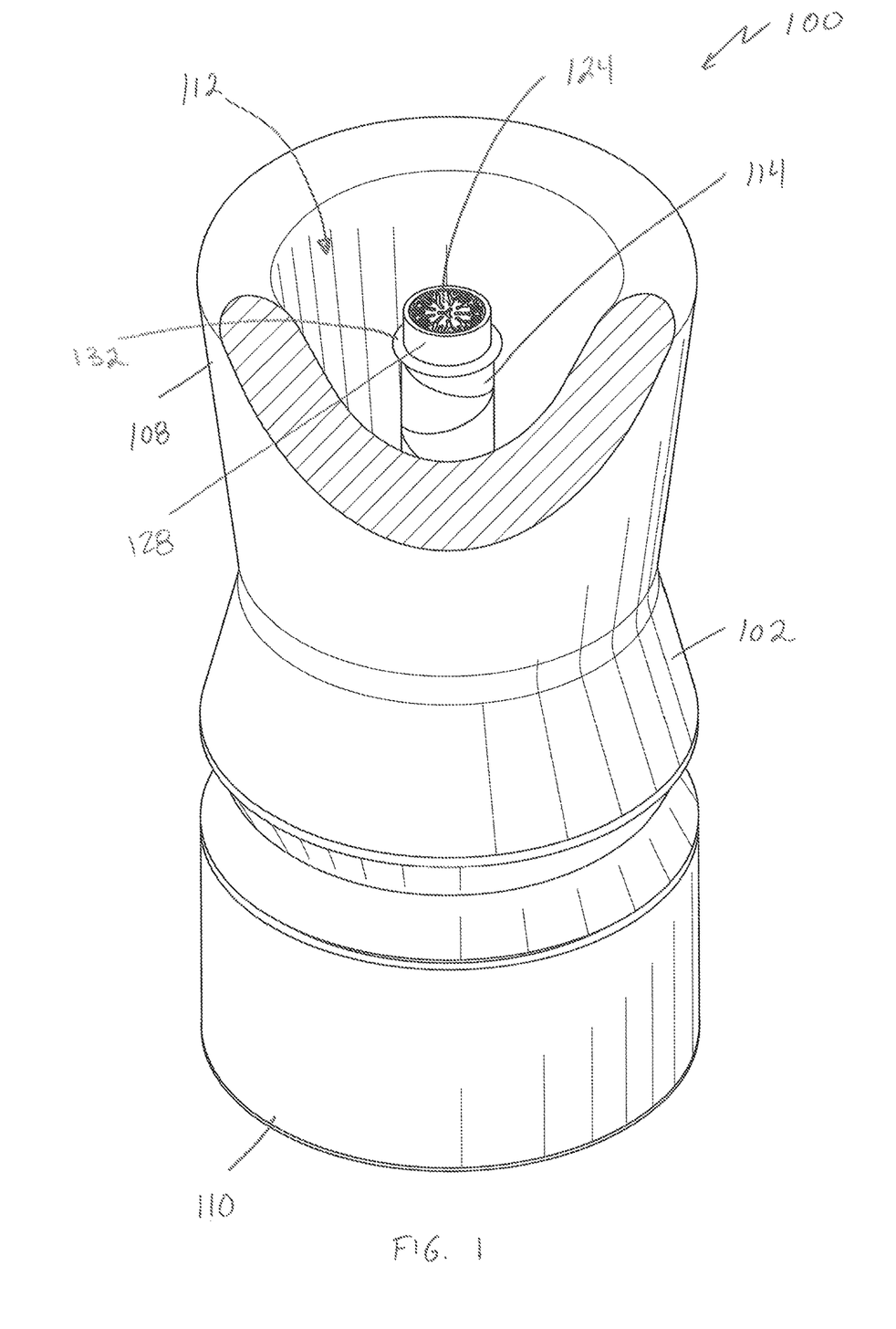
FIG. 1 is a perspective view of a convection aromatherapy device according to one or more examples of embodiments, showing a portion of the annular wall of the body cut away to reveal the heater core.
Figure 2:
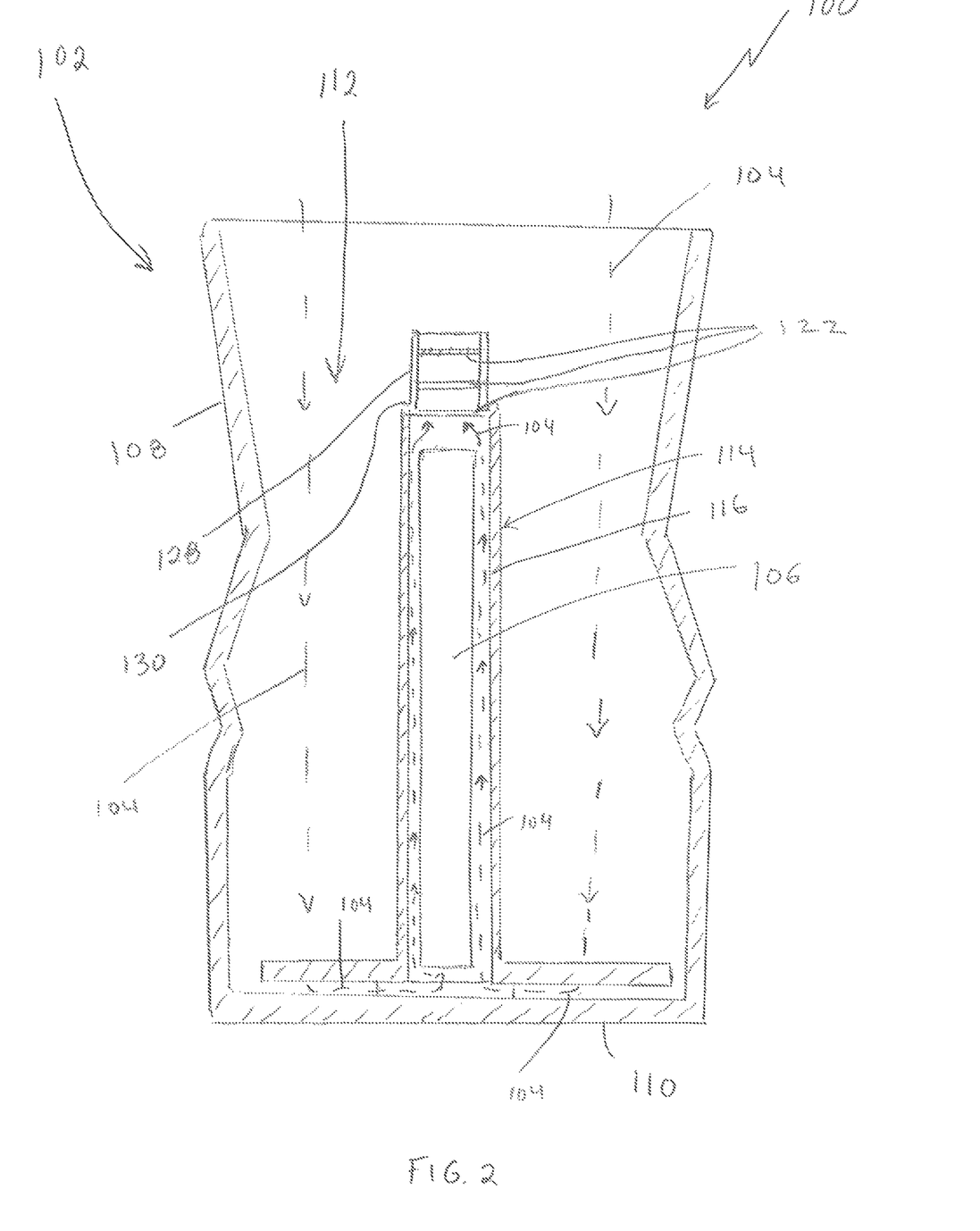
FIG. 2 is a cross-sectional view of a convection aromatherapy device according to one or more examples of embodiments, including a partial cross section of the body and a partial cross section of the heater core.
Figure 3:
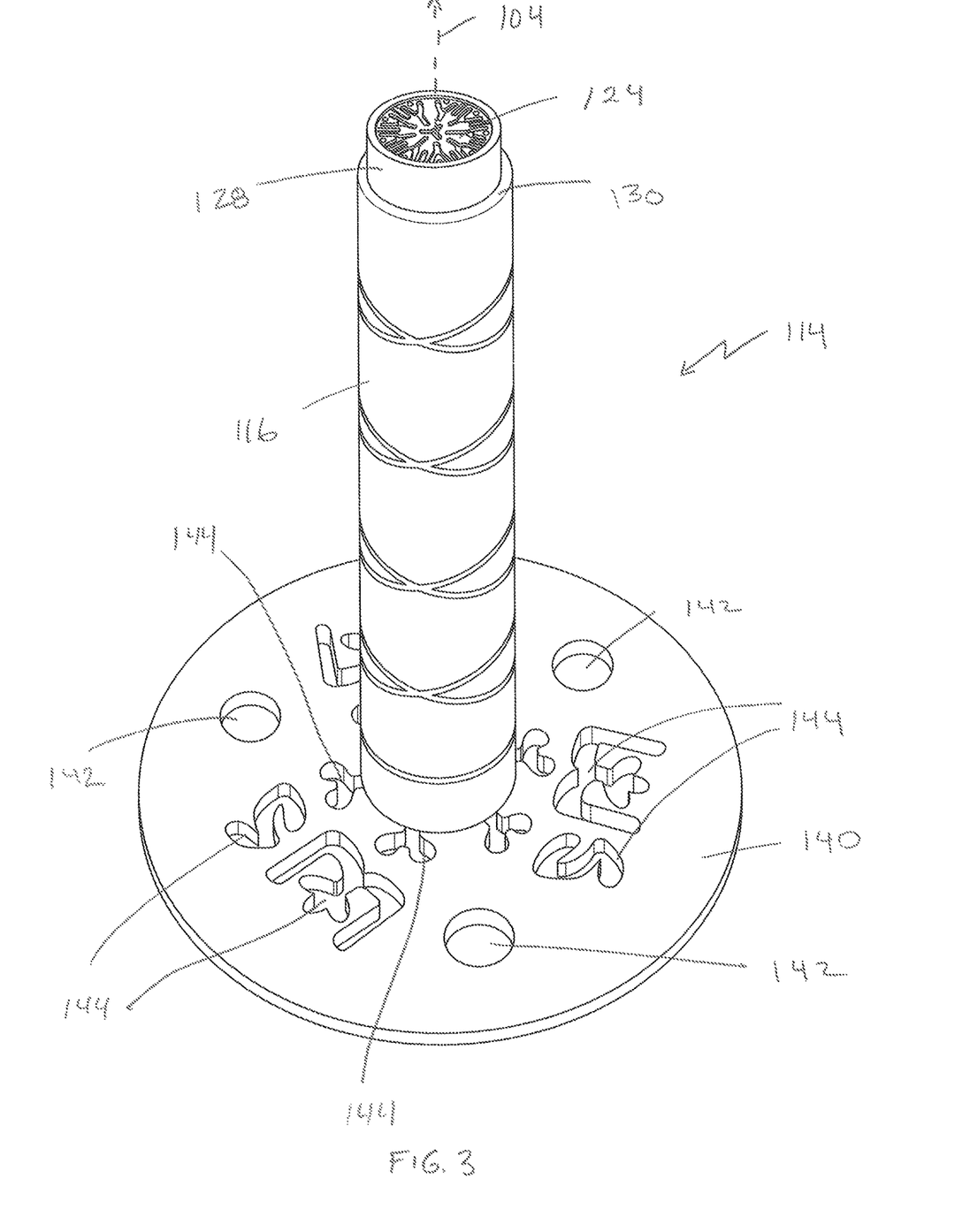
FIG. 3 is a perspective view of a heater core for use with the convection aromatherapy device in one or more examples of embodiments.
Figure 4:
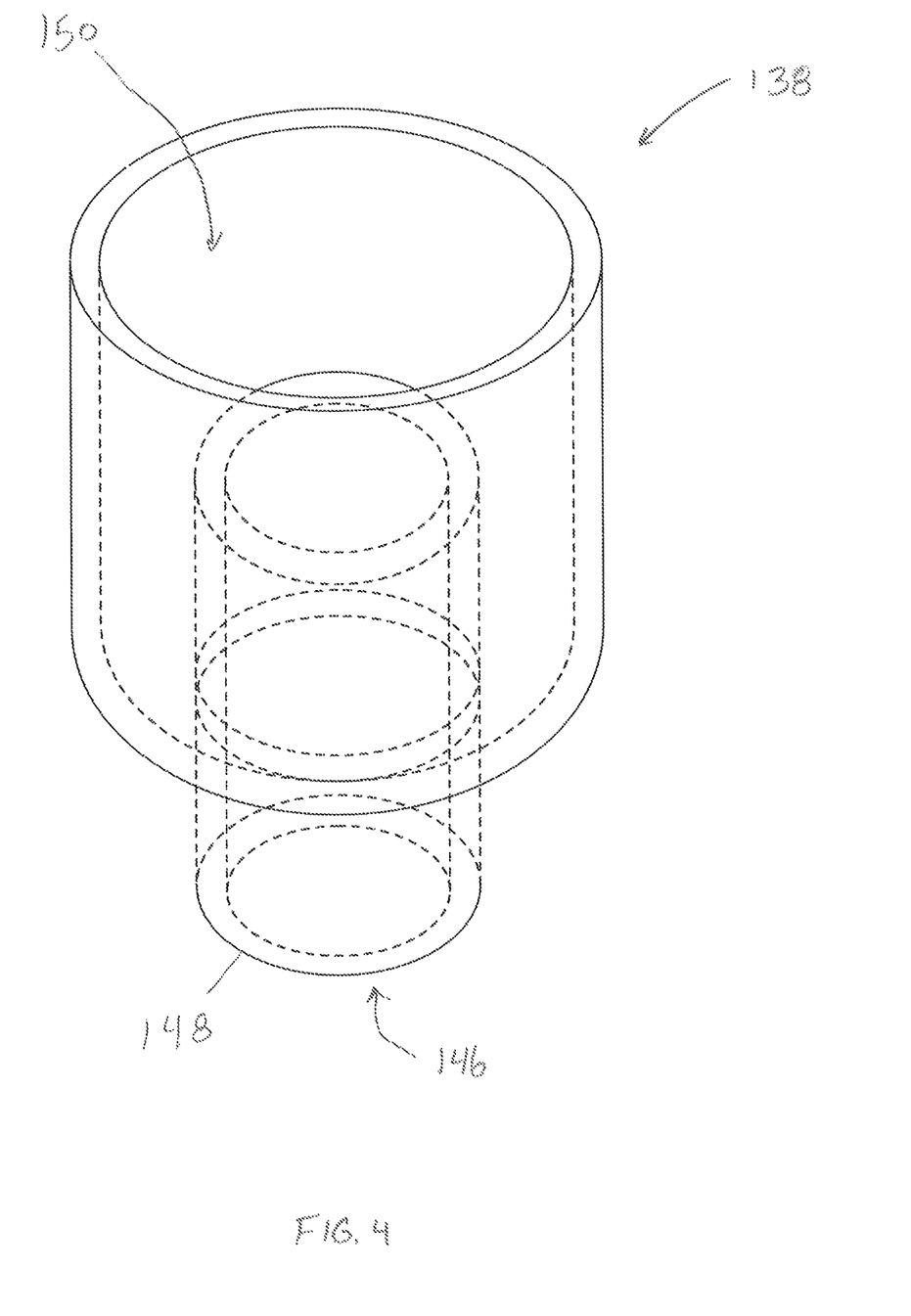
FIG. 4 is a partially transparent, perspective view of a cup or reservoir attachment for the convection aromatherapy device in one or more examples of embodiments.
Figure 5:
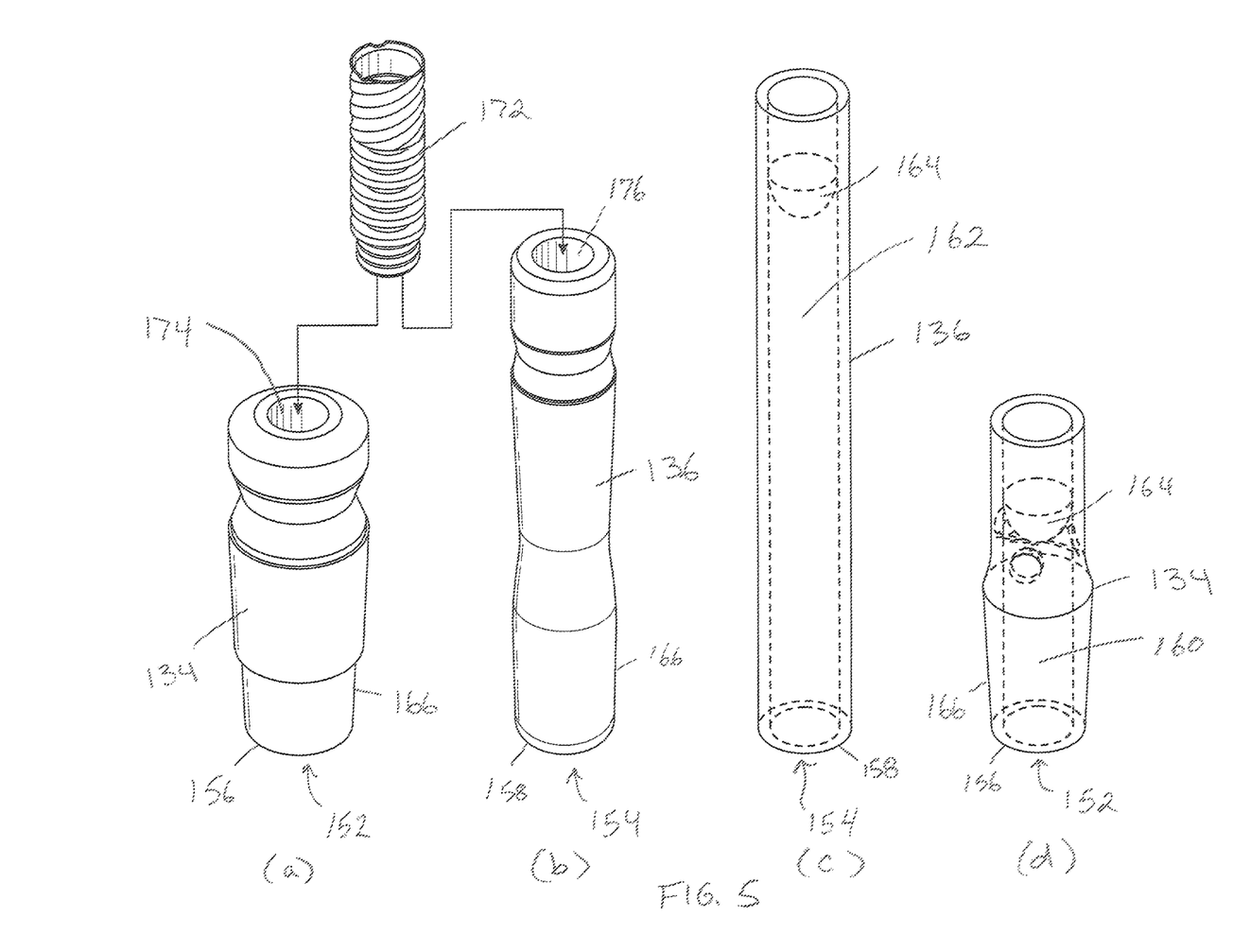
FIG. 5 shows perspective views of attachments for the convection aromatherapy device in one or more examples of embodiments, showing: (a) an example of an adapter for use with the convection aromatherapy device; (b) an example of an extension stem for use with the convection aromatherapy device; (c) an alternative example of an extension stem for use with the convection aromatherapy device, showing a partially transparent view of the device; and (d) an alternative example of an adapter for use with the convection aromatherapy device, showing a partially transparent view of the device.
Figure 6:
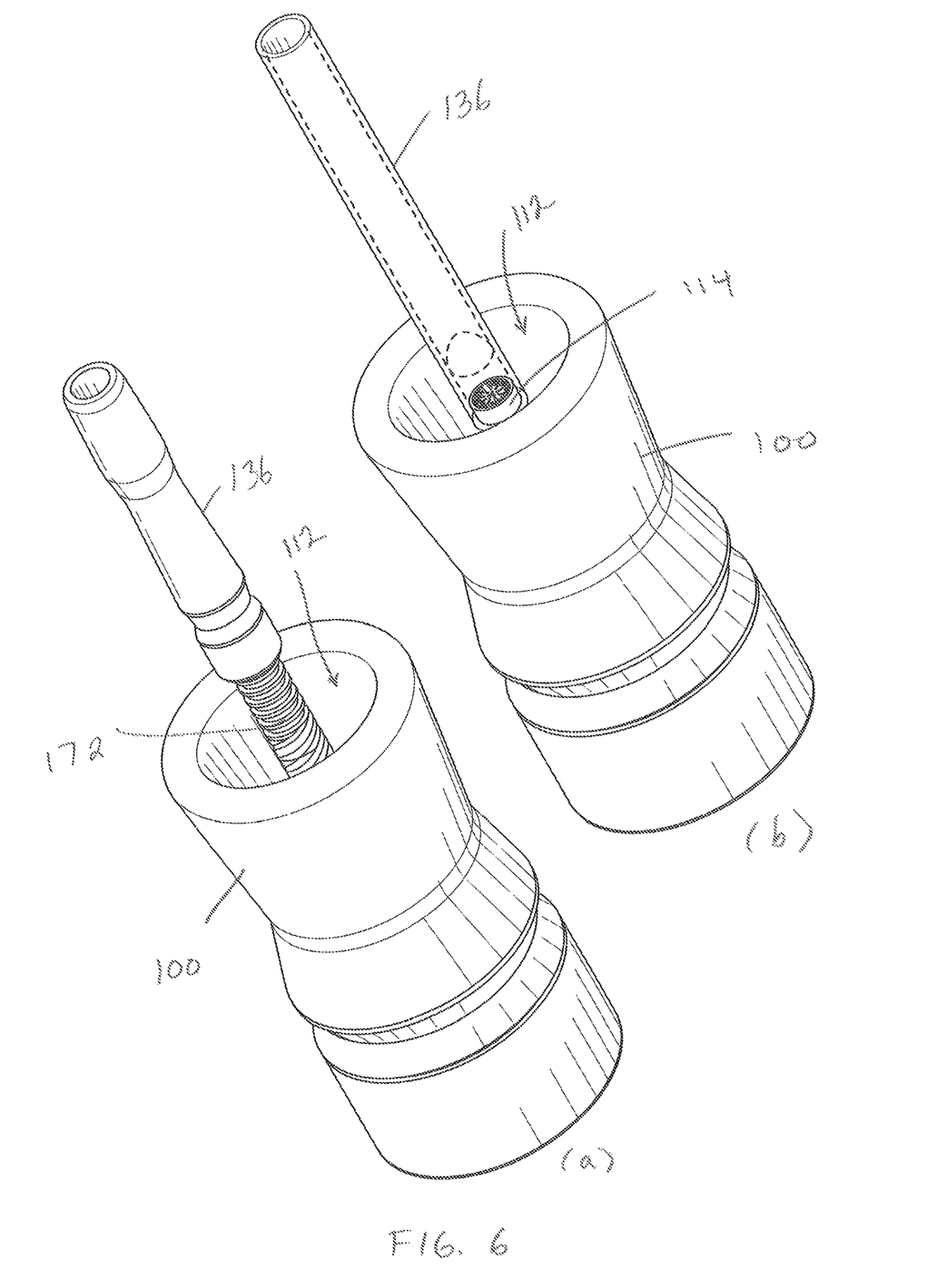
FIG. 6 shows perspective views of extension stems attached to the convection aroma therapy device in one or more examples of embodiments, showing: (a) an example of the extension stem of FIG. 5(b) attached to the convection aroma therapy device; and (b) an example of the extension stem of FIG. 5(c) attached to the convection aroma therapy device.
Figure 7:
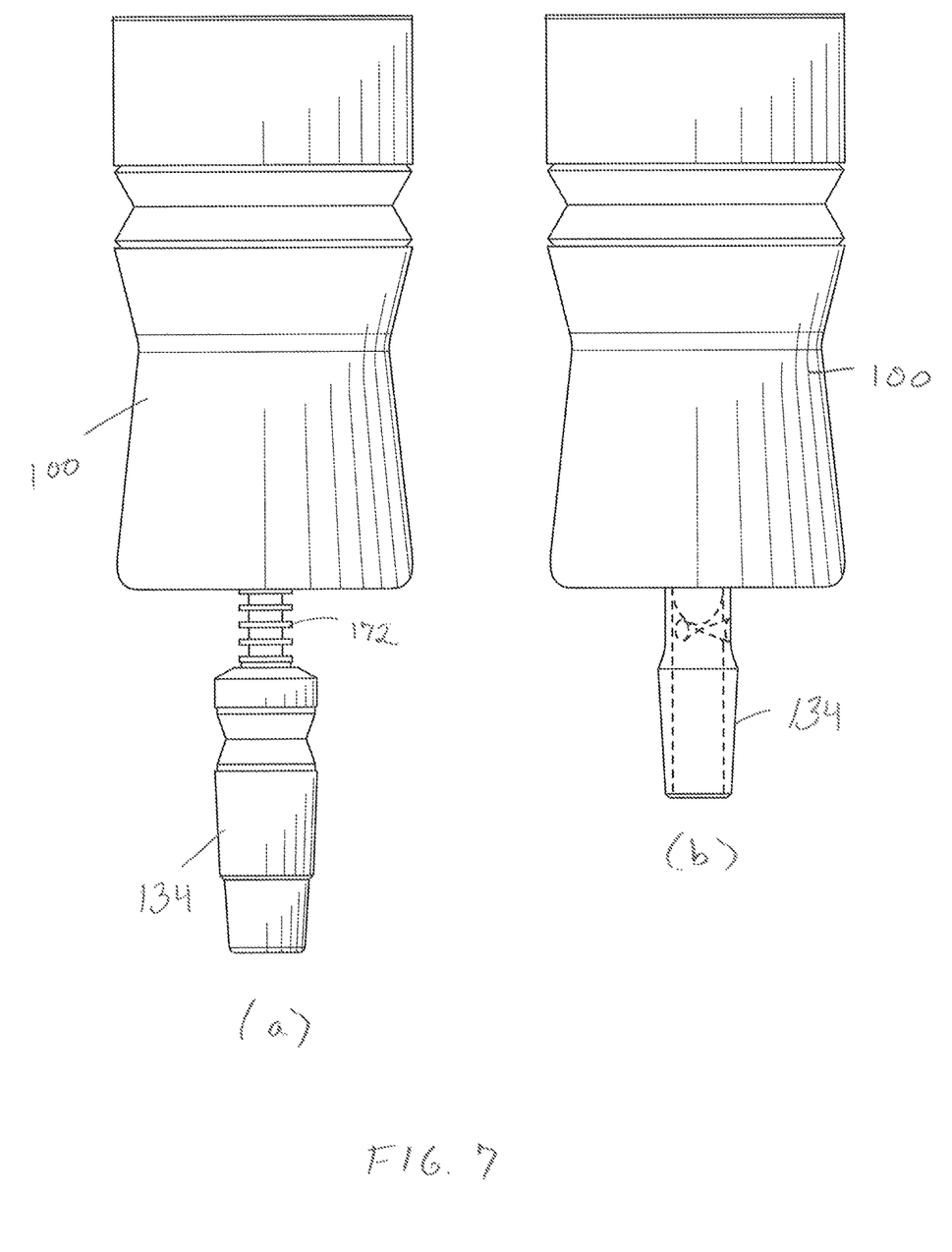
FIG. 7 shows elevation views of adapters attached to the convection aroma therapy device in one or more examples of embodiments, showing: (a) an example of the adapter of FIG. 5(a) attached to the convection aroma therapy device; and (b) an example of the adapter of FIG. 5(d) attached to the convection aroma therapy device.
Figure 8:
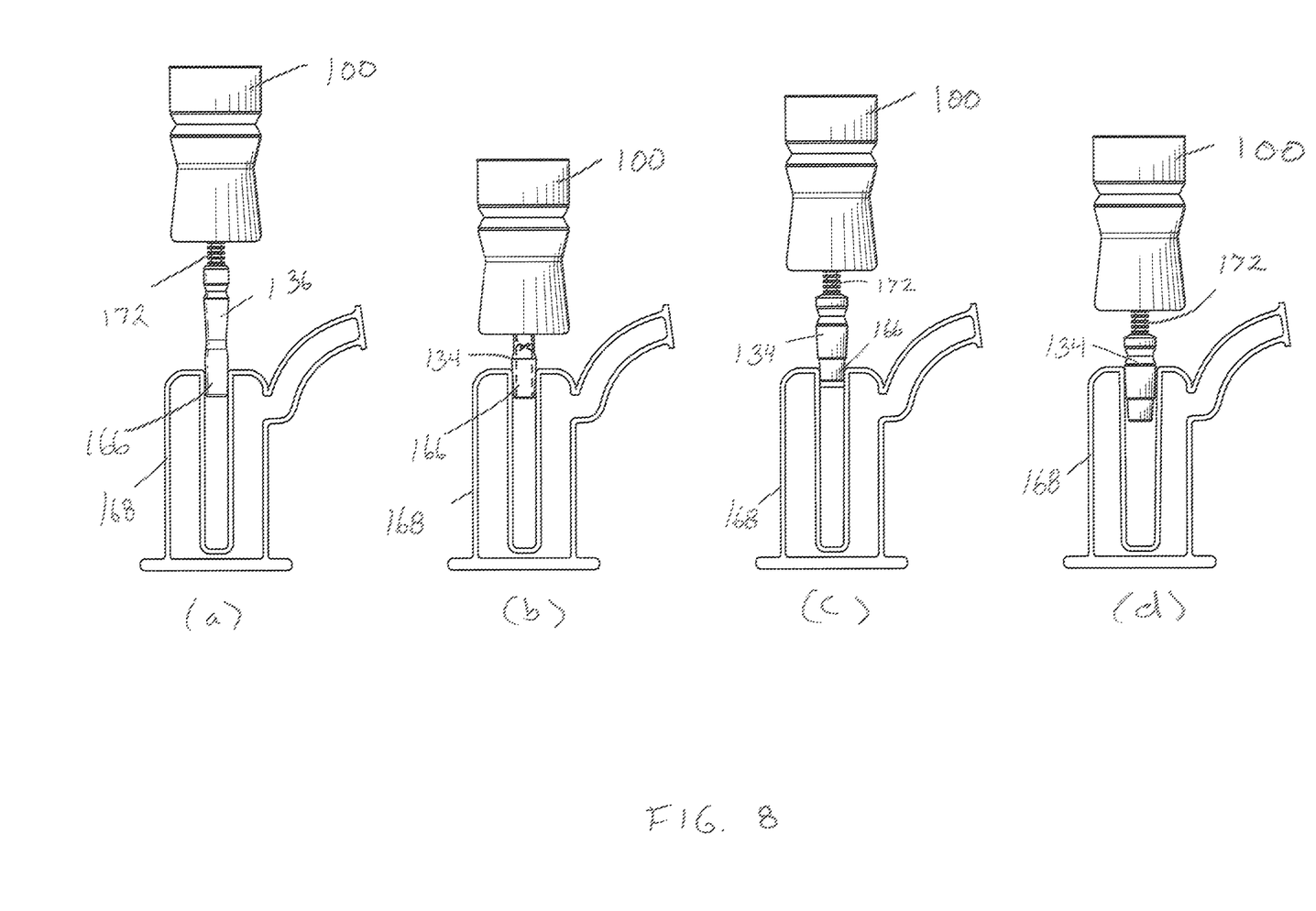
FIG. 8 shows elevation views of convection aroma therapy devices having adapters and stems attached to a water pipe shown in cross section, showing (a) the extension stem of FIG. 5(b) in use with the convection aromatherapy device; (b) the adapter of FIG. 5(d) in use with the convection aromatherapy device; (c) the adapter of FIG. 5(a) in use with the convection aromatherapy device in a first position; and (d) the adapter of FIG. 5(a) in use with the convection aromatherapy device in a second position.

Referring to FIGS. 1-3, a convection aromatherapy device 100 is shown. The convection aromatherapy device 100 generally comprises a body 102, an air path 104 for transfer of heat, and a cartridge heater 106, such as an electric cartridge heater. The body 102 is formed by an annular wall 108 and a base 110 creating a recessed area 112. Within the recessed area 112 is a heater core 114 and air path 104. In one or more examples of embodiments, a space or an interstitial space exists between the annular wall 108 or enclosure and the heater core 114, which may provide a means to insulate the annular wall 108 so a user may touch the annular wall 108 without burning his or herself. The space may also provide additional air circulation and form part of the overall air path. The body 102 may be formed of one or more of a variety of durable materials. In one example, the body 102 is formed of wood. However, plastic, stone, metal, ceramic, and other materials are also contemplated.

As indicated, the convection aromatherapy device 100 has a heater core 114 with an air path 104, an example of which is shown in FIG. 2. The air path 104 has a heat exchanger therein formed by an assembly of a heater cartridge 106 and tubular enclosure 116. More specifically, a heater cartridge 106 is provided within a small annular space formed by and/or surrounded by a tubular enclosure 116. The heater cartridge 106 is electrically powered. To this end, the heater cartridge 106 is coupleable to a power cable 118 and temperature control 120 (see FIG. 12); namely, a power cord may extend into the body 102 or into the recessed area 112. The air path 104 is defined by the cylindrical heater core 114, which is designed with a wall thickness in the heater core 114 calibrated for minimized heat loss as well as sufficient thermal mass to provide for consistent thermal transfer to the incoming airstream during short periods of significant airflow without a precipitous drop in temperature.

Figure 10:
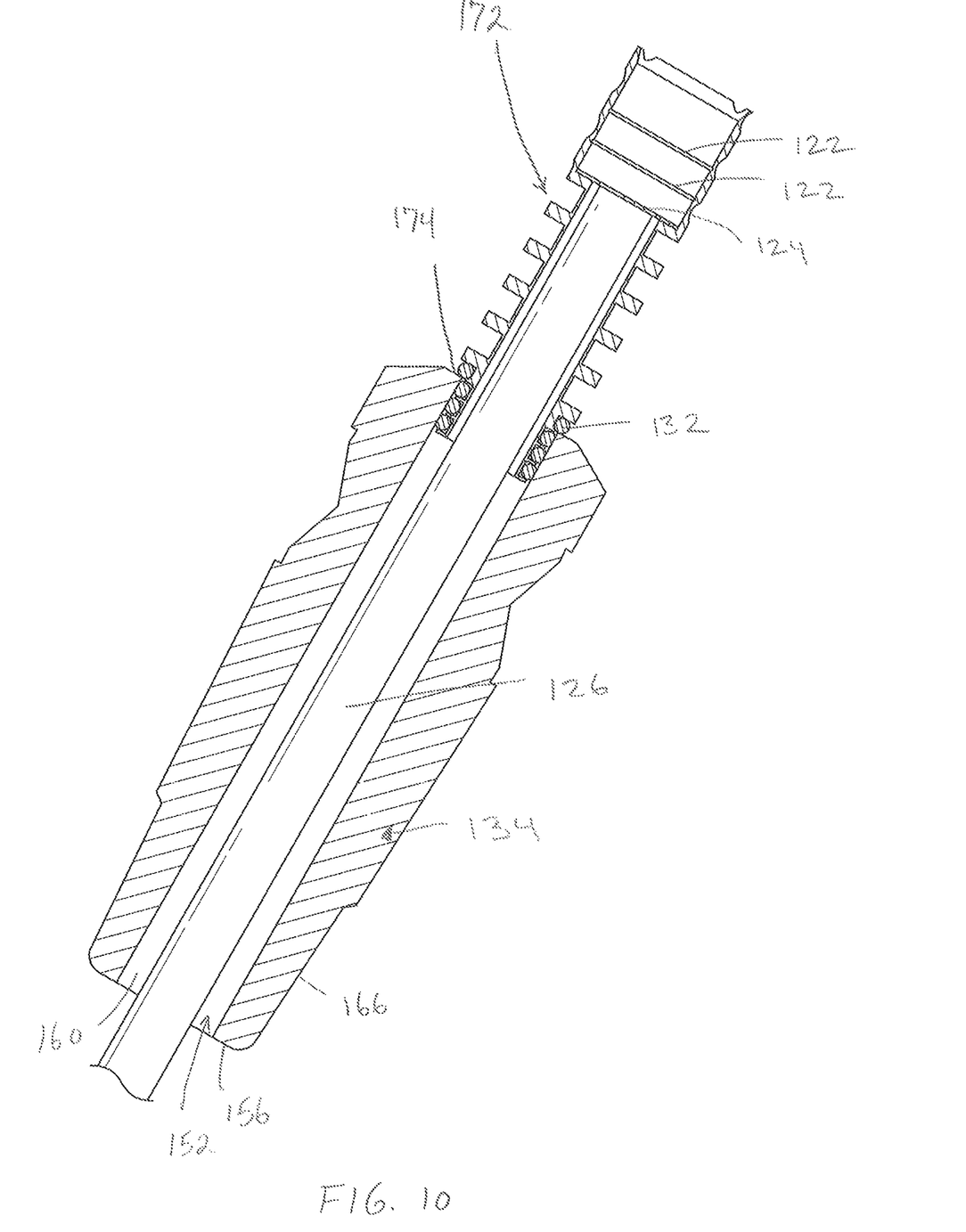
FIG. 10 shows a cross section view of an adapter having a tip and a dowel inserted into the channel of the adapter and tip.
Figure 11:
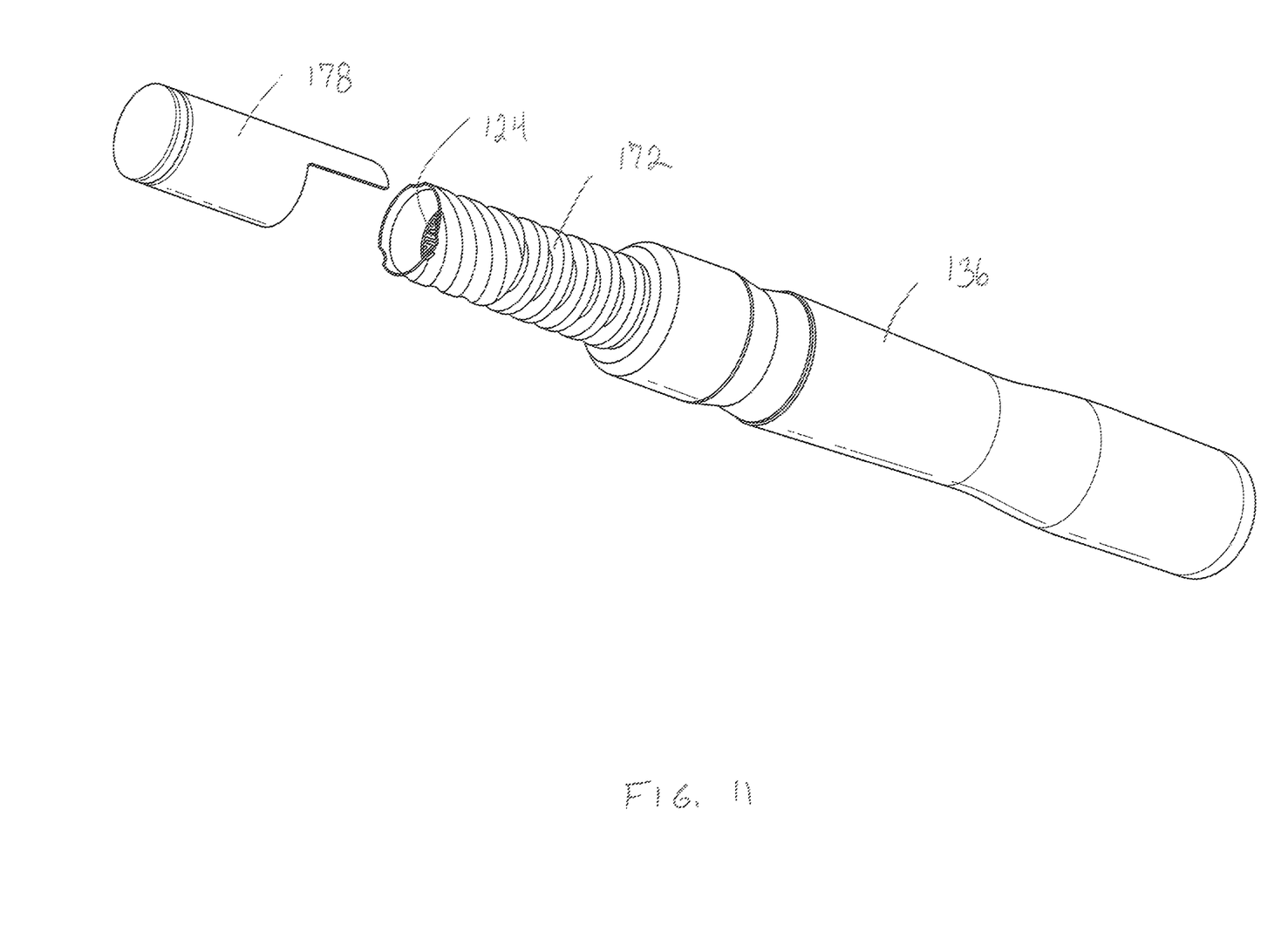
FIG. 11 is a perspective view of an extension stem and tip having a cap removed from the tip.

The heater core 114 also includes an internal groove 122, machined into an end portion of the heater core 114. A circumferential compression diffuser (CCD) 124 which is disc shaped is placed and retained in the internal groove 122. Preferably, the groove 122 is on an interior surface of the heater core 114 toward an upper end thereof. In some examples of embodiments, a plurality of grooves 122 are provided so that the CCD 124 may be moved to different positions within the air path 104. A dowel or other device 126 may be used to adjust the CCD 124 to a different one or more of the plurality of grooves 122 (note FIG. 10 shows an example of a use of a dowel 126 in connection with a CCD 124 and plurality of grooves 122 in a tip 172).

At the exit of the air path 104, namely on an upper portion of the heater core 114 or at the top of the tubular enclosure 116, is a functional geometry creating a mating mechanism 128. The mating mechanism 128 provides a means of attaching various devices to the convection aromatherapy device 100. In the illustrated examples, such as shown in FIGS. 2-3, the mating mechanism 128 comprises an area of narrowed cross-section or diameter as compared to the heater core 114 tubular enclosure 116. That is, the mating mechanism 128 is made up of a cylindrical portion having a diameter which is smaller than the diameter of the tubular enclosure 116. At the bottom of the mating mechanism 128, or its intersection with the enclosure 116 is an annular collar 130. In one or more examples of embodiments, a sealing device such as, but not limited to, an O-ring 132 may be seated on the annular collar 130 (see FIG. 1).

The mating mechanism 128 mates with one or more interior surfaces of aromatherapy accessories and/or attachments and maintains them in a constrained manner via a concentric coupling with the small annular space to allow for easy alignment, insertion and removal. For example, an adapter 134, an extension stem 136, or a cup 138 (discussed in further detail hereinbelow) may attach to the mating mechanism 128. In one or more preferred examples of embodiments, the means of attaching various devices is provided in a manner only constrained in two axis. This coupling does not restrict airflow or removal from the mating mechanism 128.

Referring to FIGS. 2-3, at the bottom end of the heater core 114 and opposite the mating mechanism 128, a disc 140 is joined to the tubular enclosure 116 which extends radially outward from the tubular enclosure 116. The disc 140 has one or more fastener holes 142, which may be used for securing to a base portion of the recessed area 112 of the body 102. The disc 140 also has one or more apertures 144, which apertures may allow for air circulation.

The heater core 114 and CCD 124 may be formed of an appropriate structural heat resistant material, such as but not limited to titanium (Ti). However, alternative materials may also be suitable for the intended purposes, such as for example, stainless steel.

As indicated and shown in reference to FIGS. 4-7, the convection aroma therapy device 100 may be used with a variety of attachments. In one example of embodiments, the body 102 may be used with a cup 138 or reservoir. The cup 138 has a receptor 146 on a bottom surface which is adapted to engage the mating mechanism 128 of the heating element or heater core 114. In one or more examples of embodiments, the bottom edge 148 of the cup receptor 146 engages the annular collar 130 of the heater core 114 so as to be secured in position on the heater core 114. The cup receptor 146 may be a stem. The cup 138 may be positioned above the top of the recessed area 112 on the body 102. Alternatively, the cup 138 may have an outer diameter which is narrower than the inner diameter of the annular wall 108 such that the cup 138 may be received within the body recessed area 112. The cup 138 also has a recessed area 150 forming a reservoir that holds a material to be heated. In one or more examples of embodiments, the cup 138 or reservoir may be formed of a durable material capable of being heated and retaining a liquid such as an oil or other material to be heated and release an aroma. In one example, reservoir is composed of glass. However, any material suitable for retaining an oil or other materials for heating and scent release may be acceptable, such as but not limited to ceramic, metal, and the like.

An extension stem 136 or adapter 134 may also be alternatively attached to the mating mechanism 128 seated within the body 102. As illustrated, the extension stem 136 and adapter 134 may take various forms, having varying lengths, widths, and other geometry. The extension stem 136 and the adapter 134 may be formed of a variety of durable materials for the purposes provided. As non-limiting examples, the extension stem 136 and/or adapter 134 may be formed of wood or glass or combinations thereof. Metal is also contemplated.

Figure 9:
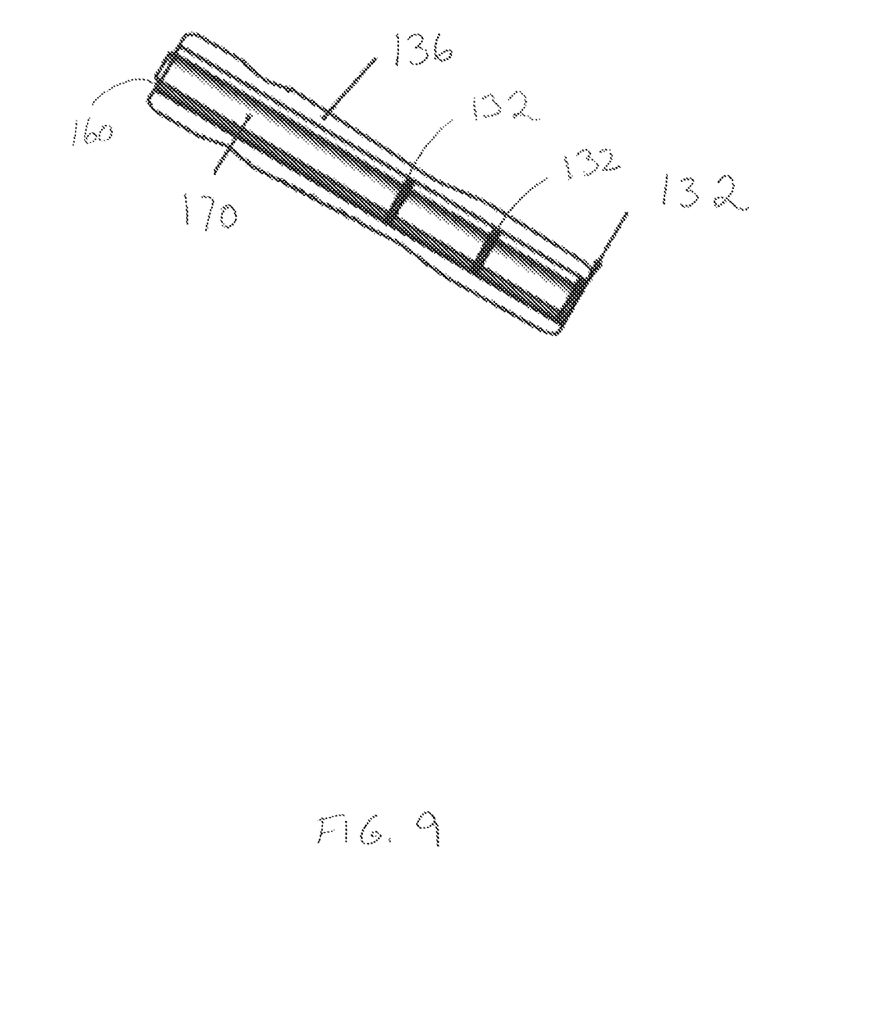
FIG. 9 shows a partial cross section view of an extension stem having a condenser therein.

Each of the extension stem 136 and the adapter 134 comprise a first end which has a receptor 152, 154 configured to attach to the mating mechanism 128. That is, the mating mechanism 128 may be received within an interior cylinder or aperture or receptor 152, 154 of the extension stem 136 and/or adapter 134 on a bottom portion thereof. The bottom edge 156, 158 of the extension stem 136 and/or adapter 134, when seated on the mating mechanism 128 may seat against or rest on the annular collar 130. In one or more preferred examples of embodiments, a sealing mechanism, such as a high-temperature O-ring 132, may be placed between the annular collar 130 and the edge 156, 158 of the extension stem 136 or adapter 134. In one or more examples of embodiments, the extension stem 136 and/or adapter 134 has an internal air path or channel 160, 162, which may be a hollow cylindrical channel. In some examples, the extension stem 136 and/or adapter 134 may have a conical screen 164 positioned within the channel 160, 162. In one or more additional examples of embodiments, the extension stem 136 and/or adapter 134 may have a tapered bottom portion 166 which is engageable or receivable in a mating device, such as but not limited to a water pipe 168 (see FIGS. 8(a)-8(d)). In one or more examples of embodiments, a condenser tube 170 may be received in the interior channel of the extension stem 136 (see FIG. 9).

An attachment, such as a cup 138 or reservoir, an extension stem 136, and/or an adapter 134 may be coupled to the heater core 114 as described herein. Additional attachments such as a water pipe or an extraction tip may be further attached. For example, one or more extraction tips or other devices available for use with exothermal vaporizers may be attached to the mating mechanism 128. In a specific example of embodiments, the mating mechanism 128 may be designed specifically to mate with one or more extraction tips 172 manufactured for use with exothermal vaporizers (see FIGS. 5(a), 5(b) & FIGS. 10-11). The top portion of the extension stem 136 and/or adapter may have a receptor 174, 176 that receives the tip. The tip may have O-rings 132 and a filter disc or CCD 124 therein. In one or more examples of embodiments, the tip 172 may be used in association with a cap 178, such as but not limited to a vaporizer cap available from Dynavap, LLC (Wisconsin).

As indicated and shown in various drawings, one or more O-rings 132 are provided at connection points between what may be a heated component and another component as a means to prevent direct thermal contact with components not designed for exposure to elevated temperatures, such as but not limited to wood components. These O-rings 132 also provide a means to create a proper seal and prevent or reduce the likelihood of leakage of air.

Figure 12:
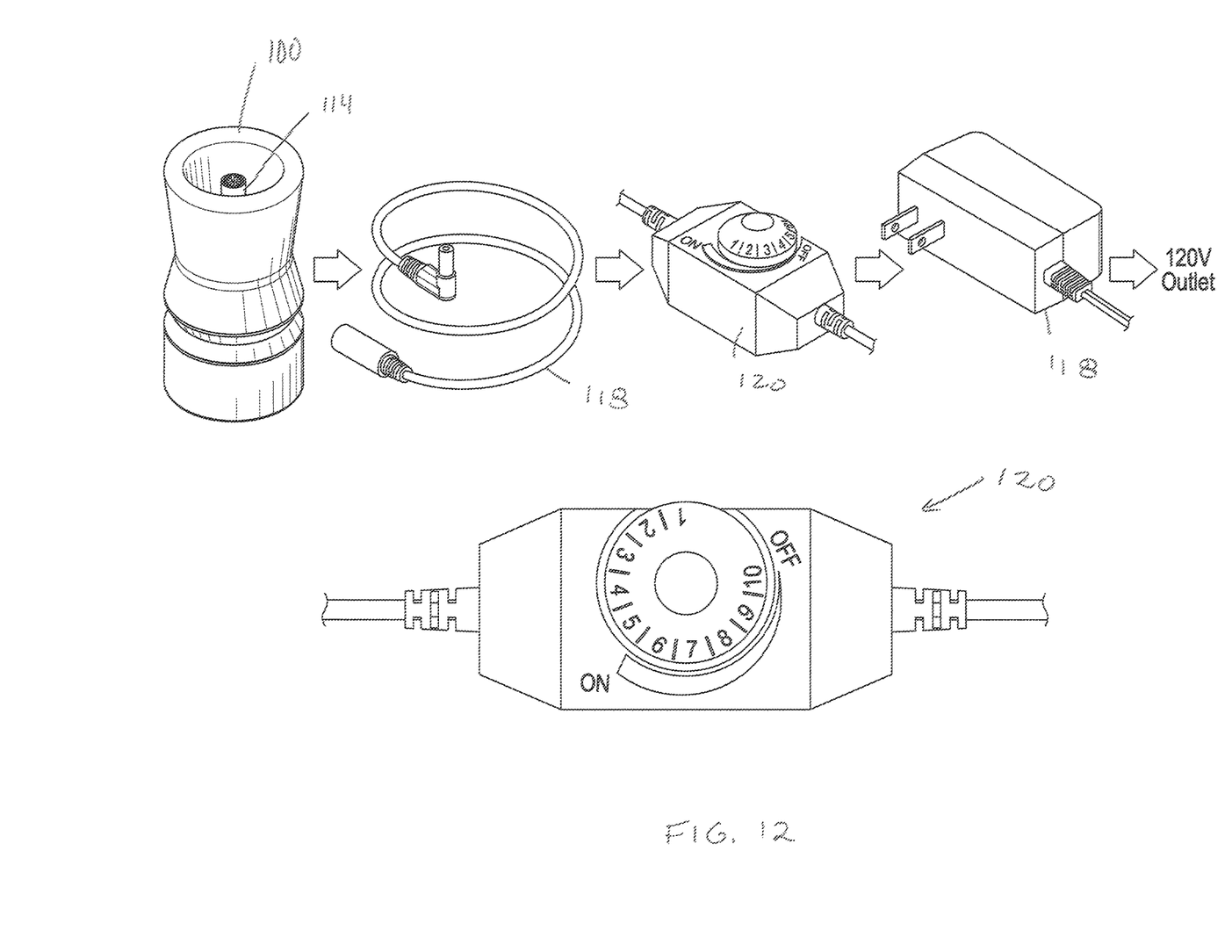
FIG. 12 is perspective view of a convection aromatherapy kit, including a convection aroma therapy device according to one or more examples of embodiments, a cable connectable to the device and a wall outlet, and a control or temperature control for the device.

Referring to FIG. 12, an electrical or temperature control 120 for a heating device 106 may be provided. The control 120 may have a range of preset temperatures corresponding to different levels of heat to be applied to the convection aroma therapy device. The levels may correspond to preferred ranges for the heating of one or more materials placed in the device. In one or more examples of embodiments, the heater core 114 is placed in the body 102, namely within the recessed area 112 such as shown in FIGS. 1-2. The heater 106 within the heater core 114 may be electrically coupled or coupleable to a corded device 118 for transmission of power to the heater 106. The use of a corded device 118 powered by a building's electrical supply alleviates some of the issues set forth above with respect to battery powered devices.

Accordingly, a kit for convection aromatherapy may be provided such as shown in FIG. 12. The kit includes a convection aromatherapy device having a body formed by an annular wall and a base creating a recessed area, a cartridge heater within the recessed area, and an air path for transfer of heat from the cartridge heater. The kit also includes a power cord coupleable to the cartridge heater for delivering power to the heater and a temperature control joined to the power cord. One or more of the attachments or attachment devices, as well as the tip and other components described herein may also be included in the kit.

In one or more examples of use of the convection aromatherapy device and kit described herein, a material to be heated is placed in the reservoir, stem, or tip. Heat is applied to the heater core 114 by activation of the heater 106. A temperature may be selected using the control device 120. The temperature may correspond to a suitable temperature for heating the selected material in the reservoir 138, stem 136, or tip 172. Heated air then travels along the air path 104. Referring to the Figures, following the airflow, when suction is applied to the convection aromatherapy device 100, ambient air enters the air path 104 flowing through the apertures 144 in the disc 140 and into an aperture in the base of the air path 104. The air then flows through an interstitial space formed by the heat resistant O-ring 132 provided between the air path 104 and the enclosure or recess formed in the body 102. Subsequently, the air enters the air path heat exchanger where there is a heater cartridge 106 with a small annular space surrounded by the tubular enclosure 116. The circumferential compression diffuser (CCD) 124 in the air path 104 functions in several regards, including but not limited to, the mixing and diffusing the hot air provided by the heat exchanger, as well as a protective device or screen to prevent unwanted debris from entering the heat exchanger. Heated air exiting the CCD 124 or top portion of the air path 104 is then applied to the attached device and/or material placed therein to be heated.

The convection aromatherapy device functions in an improved manner by, generally, re-routing an incoming airstream along a longer, more convoluted path, allowing for extended contact to significantly increase surface area for heat transfer, as well as providing a cooling effect for the components not designed for exposure to elevated temperatures. This is accomplished by incorporating one or more of several features described hereinabove not found in other devices. By utilizing an improved design for airflow and materials with better thermal properties in conjunction with thermal isolation, the described device addresses many of the shortcomings of previous devices.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that references to relative positions (e.g., "top" and "bottom") in this description are merely used to identify various elements as are oriented in the Figures. It should be recognized that the orientation of particular components may vary greatly depending on the application in which they are used.

For the purpose of this disclosure, the term "coupled" means the joining of two members directly or indirectly to one another. Such joining may be stationary in nature or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It is also important to note that the construction and arrangement of the system, methods, and devices as shown in the various examples of embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements show as multiple parts may be integrally formed, the operation of the interfaces may be reversed or otherwise varied, the length or width of the structures and/or members or connector or other elements of the system may be varied, the nature or number of adjustment positions provided between the elements may be varied (e.g. by variations in the number of engagement slots or size of the engagement slots or type of engagement). The order or sequence of any process or method steps may be varied or re-sequenced according to alternative embodiments. Other substitutions, modifications, changes and omissions may be made in the design, operating conditions and arrangement of the various examples of embodiments without departing from the spirit or scope of the present inventions.

While this invention has been described in conjunction with the examples of embodiments outlined above, various alternatives, modifications, variations, improvements and/or substantial equivalents, whether known or that are or may be presently foreseen, may become apparent to those having at least ordinary skill in the art. Accordingly, the examples of embodiments of the invention, as set forth above, are intended to be illustrative, not limiting. Various changes may be made without departing from the spirit or scope of the invention. Therefore, the invention is intended to embrace all known or earlier developed alternatives, modifications, variations, improvements and/or substantial equivalents.

The technical effects and technical problems in the specification are exemplary and are not limiting. It should be noted that the embodiments described in the specification may have other technical effects and can solve other technical problems.

The invention claimed is:

1. A convection aromatherapy device comprising:
a body formed by an annular wall and a base creating a recessed area;
a heater core with an air path, the air path having a heat exchanger therein formed by an assembly of a cartridge heater and a tubular enclosure surrounding the cartridge heater, the heater core being provided within the recessed area and spaced from the annular wall;
wherein the air path is configured to transfer heat from the cartridge heater;
wherein the heater core comprises a disc joined to the tubular enclosure and extending radially outward from the tubular enclosure; and
wherein the disc has one or more apertures that allow for air circulation.

2. The convection aromatherapy device of claim 1, wherein a circumferential compression diffuser is retained in the heater core.

3. The convection aromatherapy device of claim 1, wherein the heater core comprises a portion having a narrowed cross section and collar, wherein said portion is configured to constrain a mating device.

4. A convection aromatherapy device assembly comprising the convection aromatherapy device of claim 3, and the mating device, wherein the mating device is selected from the group consisting of a reservoir, an adapter, and an extension stem, said mating device being coupled to the portion.

5. The assembly of claim 4, wherein the mating device is an adapter or an extension stem, and further comprising a tip joined thereto.

6. The convection aromatherapy device of claim 1, wherein an interstitial space exists between the annular wall and the heater core.

7. The convection aromatherapy device of claim 1, wherein the cartridge heater is disposed within the air path.

8. The convection aromatherapy device of claim 1, wherein the disc includes one or more fasteners for securing the disc to the base portion in the recessed area.

* * * * *